(12) United States Patent
Tran et al.

(10) Patent No.: US 6,482,968 B1
(45) Date of Patent: Nov. 19, 2002

(54) PURIFICATION OF AN ORGANOMETALLIC COMPOUND

(75) Inventors: Nam H. Tran, Pasadena; Joseph N. Christopher, League City; Timothy J. Michalec, Needville, all of TX (US)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/980,044
(22) PCT Filed: May 17, 2000
(86) PCT No.: PCT/US00/13566
§ 371 (c)(1),
(2), (4) Date: Feb. 7, 2000
(87) PCT Pub. No.: WO00/71551
PCT Pub. Date: Nov. 30, 2000

Related U.S. Application Data
(60) Provisional application No. 60/135,376, filed on May 21, 1999.

(51) Int. Cl.$^7$ .................................................. C07F 5/06
(52) U.S. Cl. ......................................................... 556/187
(58) Field of Search .......................................... 556/187

(56) References Cited

U.S. PATENT DOCUMENTS

| | | | | |
|---|---|---|---|---|
| 3,627,808 A | * | 12/1971 | Streck | 556/129 |
| 4,013,421 A | | 3/1977 | Bagdasarov et al. | 23/273 SP |
| 4,362,560 A | | 12/1982 | Abrjutin et al. | 75/63 |
| 4,650,895 A | | 3/1987 | Kadokura et al. | 556/182 |
| 4,720,561 A | | 1/1988 | Bradley et al. | 556/1 |
| 4,797,500 A | | 1/1989 | Kadokura et al. | 556/1 |
| 4,847,399 A | | 7/1989 | Hallock et al. | 556/1 |
| 5,455,364 A | | 10/1995 | Yako et al. | 556/1 |
| 5,951,820 A | | 9/1999 | Ohsaki et al. | 159/47.1 |

FOREIGN PATENT DOCUMENTS

| | | |
|---|---|---|
| GB | 1051830 | * 12/1966 |
| GB | 2123423 | 2/1984 |
| GB | 2201418 | 9/1988 |
| JP | 8-12678 | 1/1996 |
| WO | 93/10125 | 5/1993 |

OTHER PUBLICATIONS

R. Tyagi et al., "High Purity Metalorganic Compounds for III–V MOCVD", Mat. Res. Bull., vol. 27, pp. 623–628 (1992).
Chemical Abstracts 106:84687 (1985).
Chemical Abstracts 124:317467 (1996).

* cited by examiner

Primary Examiner—Porfirio Nazario-Gonzalez
(74) Attorney, Agent, or Firm—Richard P. Fennelly

(57) ABSTRACT

Organometallic compounds, as exemplified by trimethylaluminum, can be purified by recrystallization from a solvent by cooling. The organometallic compound is first dissolved in a solvent forming a solution and the purified organometallic compound is then recrystallized, under cooling conditions, from the solvent.

8 Claims, 1 Drawing Sheet

TMAL Zone Crystallizer

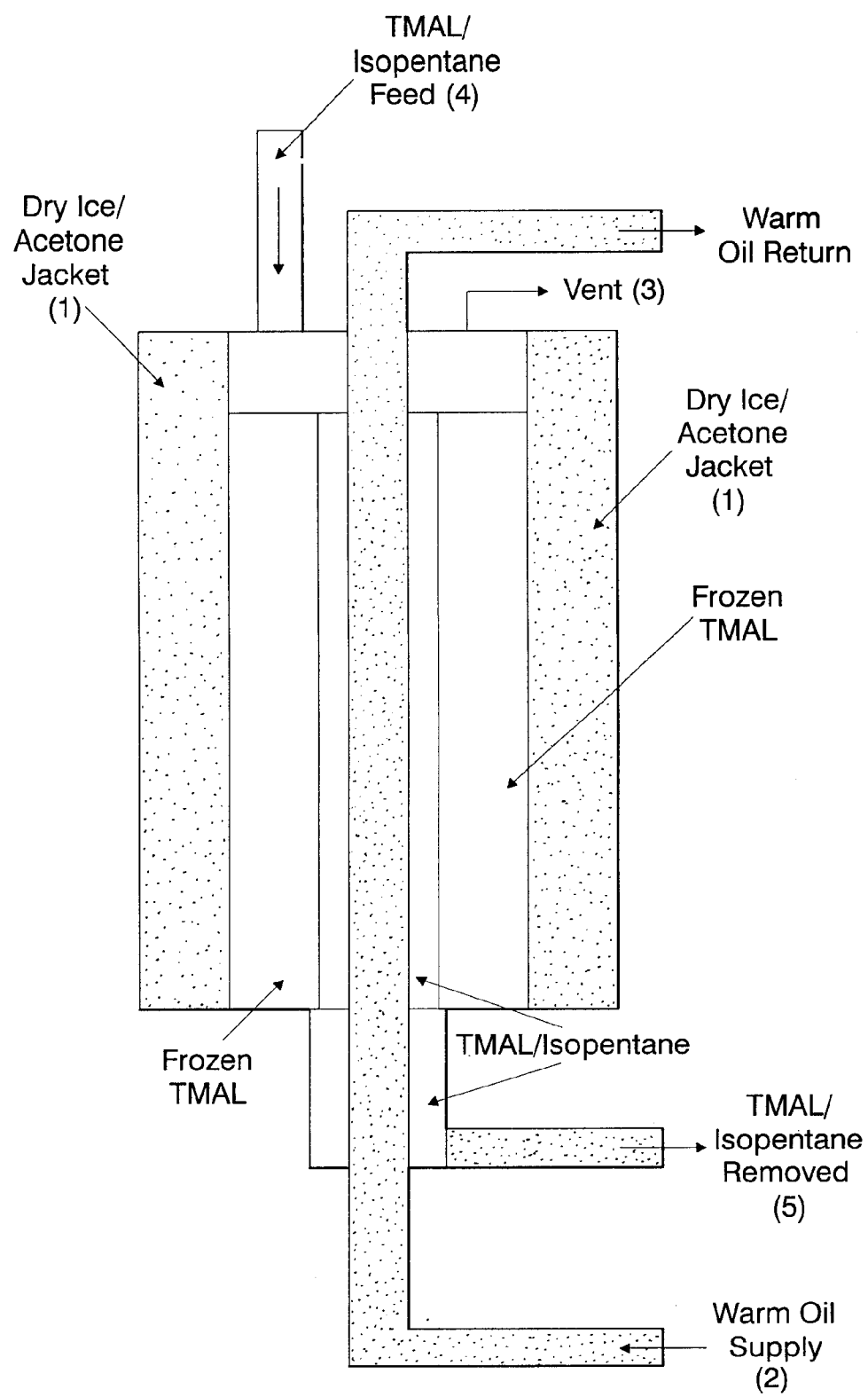
TMAL Zone Crystallizer

PURIFICATION OF AN ORGANOMETALLIC COMPOUND

This application claims priority from Provisional application Ser. No. 60/135,376, filed May 21, 1999.

BACKGROUND OF THE INVENTION

Various disclosures exist that describe several types of techniques that have been employed for the purification of organometallic compounds, such as trimethylaluminum, including the following:

Japanese Patent Publication No. 08/12,678 describes the use of a cooling tube to precipitate, from a melt composition of an organometallic compound, the desired organometallic compound in purified form. This technique treats a neat composition of the organometallic compound that is to be purified.

Apparatus that are especially designed for directional crystallization are described as being suitable for the purification of an organometallic compound in Chemical Abstracts, Vol. 106, 84687 (1999).

U.S. Pat. No. 4,362,560 describes the use of a vacuum-thermal decomposition procedure to produce high purity gallium from gallium-arsenic containing waste.

Adduct formation between the organometallic compound and an adduct-forming reagent followed by later dissociation by thermal means is described in PCT International Patent Publication Nos. WO 85/04405 and WO 93/10125, British Patent Nos. 2,123,423 and 2,201,418, and U.S. Pat. Nos. 4,720,561 and 4,847,399.

SUMMARY OF THE INVENTION

The present invention relates to a recrystallization technique for the purification of an organometallic compound in which the organometallic compound is recrystallized, under cooling conditions, from a solvent containing the organometallic compound.

DESCRIPTION OF THE PREFERRED EMBODIMENTS

The present invention, while being described with particular reference to the purification of trimethylaluminum (TMAL), is also useful with other organometallic compounds, such as, but not limited to, the trialkyl compounds of aluminum, gallium or indium containing from one to about four carbon atoms in the alkyl group(s).

A common way in which TMAL, for example, is prepared is by the following reactions, conducted in batch (where Me signifies methyl and Et signifies ethyl):

$2Al+3MeCl \rightarrow Me_3Al_2Cl_3$ $2Me_3Al_2Cl_3+2Et_3Al \rightarrow 3Me_2AlCl+3Et_2AlCl$ $3Me_2AlCl+3Na \rightarrow 2Me_3Al+3NaCl+Al$ The TMAL product from the above type of reaction will typically contain, for example, from about 50 to 20 about 200 ppm of silicon as an impurity due to the presence of such an impurity from the triethylaluminum and the methylaluminum-sesquichloride reagents that are employed in that process. The ultimate source of this impurity is from the aluminum powder that is used in the processes that are employed in making the triethylaluminum and methylaluminum-sesquichloride.

It has been found possible to purify the TMAL product of such impurity component, for example, by dissolving it in a suitable hydrocarbon solvent, such as iso-pentane, hexane, or heptane, and then cooling the resulting solution to a temperature of about 0° C. or below to force the recrystallization of the TMAL out of the solution. The recrystallization procedure can be advantageously practiced at pressures ranging from low vacuum to moderate pressure (for example, from about 0 psia to about 45 psia). It is essential to the use of the present invention that the crystallization temperature of the organometallic compound (such as TMAL) needs to be higher than the solidification temperature of the selected solvent. Since the silicon impurities, for example, are apparently present in the TMAL as nonassociated and non-complexed silanes, these impurities will largely remain in the solvent, for example, after the TMAL has recrystallized from it. The liquor containing the impurities is then separated from the TMAL crystals either by decantation or filtration, and the recovered TMAL crystals can be washed with fresh solvent. The final step is, preferably, the melting and distillation of TMAL to remove the last traces of solvent from it.

The following Examples further illustrate the present invention.

EXAMPLE 1

Silicon removal from TMAL via crystallization from an iso-pentane solution (1 cycle) is illustrated in this Example. TMAL (393 g), containing approximately 60 ppm Si, was added to a 1 liter jacketed reactor under a nitrogen atmosphere. Iso-pentane (101 g) was then added, and the solution was mixed. The mixer was shut off, and the reactor was then cooled to a temperature of −23.5° C. over two hours. At this temperature, only the TMAL was frozen. The residual solution (about 100 ml) was then drained out the bottom of the reactor. The reactor was then warmed to room temperature, and the TMAL in the reactor was sampled. ICP analysis of the sample determined that the silicon content had been reduced to 17.1 ppm.

EXAMPLE 2

Silicon removal from TMAL via crystallization from an iso-pentane solution (2 cycles) is shown in this Example. TMAL (414 g), containing approximately 60 ppm Si, was added to a 1 liter jacketed reactor under a nitrogen atmosphere. Iso-pentane (190 g) was then added, and the solution was mixed. The mixer was shut off, and the reactor was then cooled to a temperature of −26° C. over two hours. The residual solution (about 90 ml) was then drained out the bottom of the reactor. The reactor was allowed to sit at low temperature for several hours, and the residual liquid (about 200 ml) was drained again. The reactor was then warmed to room temperature, and the TMAL in the reactor was sampled. Additional iso-pentane (220 g) was added to the reactor, and the solution was mixed for several minutes. The reactor was then cooled to a temperature of −28° C. over two hours. The residual solution (about 200 ml) was then drained out the bottom of the reactor. The reactor was allowed to sit at low temperature for several hours, and the residual liquid (about 175 ml) was drained again. The reactor was then warmed to room temperature, and the TMAL in the reactor was sampled. ICP analysis of the samples determined that the silicon content had been reduced to 10.4 ppm after the first crystallization cycle and further reduced to 3.4 ppm after the second crystallization cycle.

COMPARATIVE EXAMPLE 3

In this Example, TMAL (97.85 g), containing approximately 60 ppm Si, was transferred into a 175 ml heavy walled capped test tube under a nitrogen atmosphere. The test tube was lowered 80% into a dry ice/acetone bath. When 80–90% of the TMAL appeared frozen, the remaining liquid (13.88 g) was removed via cannula. The TMAL was allowed to melt and was sampled. The test tube was again lowered 80% into a dry ice/acetone bath. When 80–90% of the TMAL appeared frozen, the remaining liquid (8.09 g) was removed via cannula. The remaining TMAL was allowed to melt and was sampled. ICP analysis of the samples determined that the silicon content was only reduced to 57.1 ppm after the first crystallization cycle and was further reduced to 42.6 ppm after the second crystallization cycle.

COMPARATIVE EXAMPLE 4

This Example illustrates silicon removal from TMAL by distillation.

TMAL (1,868.2 g), containing 60 ppm Si, was added to a 1-gallon glass reaction vessel, which was part of a distillation apparatus that also contained a 51 inch packed distillation column and condenser. Under a nitrogen atmosphere, the TMAL was distilled at approximately 800 Torr. Using a 20:1 reflux-to-make ratio, a 20% forecut was taken with the overhead temperature between 102° C. and 126° C. The reflux-to-make ratio was then set to 1:1 for the remainder of the distillation that produced approximately 1300 g of product (70%) at 126° C.–127° C. ICP analysis of the product determined that the silicon content was lowered to 6.3 ppm.

EXAMPLE 5

This Example also illustrates silicon removal from TMAL by crystallization Using a 1-gallon reaction vessel under nitrogen atmosphere and at room temperature (25° C.), hexane (992.0 g) was added to a solution of TMAL (1,308 g) containing 60 ppm Si. After mixing the solution for five minutes, the reaction slurry was cooled to −46.6° C. over a period of approximately two hours using a dry ice acetone bath. At this temperature, the reaction vessel contained a frozen mass of TMAL covered by a liquid layer of hexane. The liquid portion (632.9 g) was removed from the vessel and was discarded. The reactor was then warmed to room temperature, at which point hexane (911.0 g) was added again. The solution was then cooled as before to −45.2° C. The liquid portion (1,443.0 g) was removed again from the frozen TMAL, and the reaction vessel warmed to room temperature at which point a sample of the TMAL was taken. The crystallization process was repeated for a third time. Hexane (604.0 g) was added, and the solution was cooled to −53.3° C. The liquid portion (586.7 g) was removed from the frozen TMAL. The slurry in the reaction vessel was warmed to room temperature, and a sample was taken. ICP analysis of the samples indicated that the silicon content had been lowered to 13.45 ppm and 1.56 ppm after the second and third crystallization cycles, respectively. After distillation of the crystallization product, the silicon level was lowered to 0.80 ppm.

EXAMPLE 6

This Example also illustrates silicon removal from TMAL using a simple 1 gallon crystallizer as shown in the Drawing, which forms a part of the present specification.

The 1 gallon crystallizer that is shown in the Drawing comprises: 1) an open dry ice/acetone jacket; 2) an internal center straight tube for heating oil; 3) a vent; 4) a liquid charge port; and 5) a bottoms valve for product removal. In accordance with the present Example, TMAL (2200 g, 3000 ml) containing 7 ppm Si and isopentane (400ml) were transferred into the crystallizer. The TMAL and isopentane were well mixed by bubbling nitrogen through the bottom valve (5). While the tempered heating oil (40° C.) was circulating through the internal tube, the ouside open jacket was then filled up with dry ice and acetone (−79° C.). The TMAL was allowed to freeze out of the TMAL/isopentane solution. After an hour of cooling, the unfrozen TMAL/isopentane (400 cc) was removed from the crystallizer. The crystallized TMAL was then washed with fresh isopentane (200 cc), and the isopentane wash was removed after thirty minutes of cooling. The washing is repeated twice. After the washes, crystallized TMAL was allowed to be melted overnight. The purified TMAL (2900 cc) was then fractionally distilled to remove isopentane residue. After distillation, the recovered TMAL (2470 cc) contained 0.6 ppm Si.

The foregoing Examples merely illustrate certain embodiments of the present invention and, for that reason, should not be construed in a limiting sense. The scope of protection that is sought is set forth in the Claims that follow.

We claim:

1. A process for the purification of a trialkyl group-containing organometallic compound having from one to about four carbon atoms in the alkyl groups which comprises cooling a solution of the organometallic compound in a solvent to cause the crystallization of the organometallic compound from the solvent.

2. A process as claimed in claim 1 wherein the compound is a trialkyl compound of aluminum.

3. A process as claimed in claim 2 wherein the compound is trimethylaluminum.

4. A process as claimed in any of claims 1–3 wherein the solvent is a hydrocarbon solvent.

5. A process as claimed in any of claims 1–3 wherein the solvent is a hydrocarbon solvent and the solution is cooled to a temperature of below 0° C.

6. A process as claimed in any of claims 1–3 wherein, after cooling, the solvent, which contains impurities, is separated from the crystallized, purified compound by either decantation or filtration.

7. A process as claimed in claim 6 wherein the crystallized, purified compound is washed with fresh solvent.

8. A process as claimed in claim 6 wherein the crystallized, purified compound is washed with fresh solvent and is then melted and distilled to further purify it.

* * * * *